US006863654B2

(12) United States Patent
Zappala et al.

(10) Patent No.: US 6,863,654 B2
(45) Date of Patent: Mar. 8, 2005

(54) URETHRAL IDENTIFICATION SYSTEM AND METHOD OF IDENTIFYING A PATIENT'S URETHRAL ANATOMIC COURSE IN REAL TIME FOR THE PRECISE PLACEMENT OF A PROSTATE TREATMENT ELEMENT

(75) Inventors: Stephen M. Zappala, Andover, MA (US); Jim Sellers, Newburyport, MA (US); Keith Rubin, Fort Lauderdale, FL (US)

(73) Assignee: Seedlings Life Science Ventures, LLC., New York, NY (US)

( * ) Notice: Subject to any disclaimer, the term of this patent is extended or adjusted under 35 U.S.C. 154(b) by 0 days.

(21) Appl. No.: 10/439,271

(22) Filed: May 15, 2003

(65) Prior Publication Data

US 2004/0225216 A1 Nov. 11, 2004

Related U.S. Application Data

(60) Provisional application No. 60/469,213, filed on May 10, 2003.

(51) Int. Cl.[7] .................................................. A61B 8/00
(52) U.S. Cl. ....................................................... 600/439
(58) Field of Search ................................. 600/407–472; 604/48, 57, 96.01, 502, 514; 128/916

(56) References Cited

U.S. PATENT DOCUMENTS

| 6,083,166 | A | * | 7/2000 | Holdaway et al. | ............ | 600/439 |
| 6,217,518 | B1 | * | 4/2001 | Holdaway et al. | ............ | 600/443 |
| 6,364,855 | B1 |   | 4/2002 | Zappala |   |   |
| 6,582,368 | B2 | * | 6/2003 | Holdaway et al. | ............ | 600/443 |

OTHER PUBLICATIONS

Michael J. Zelefsky, M.D., et al., "Dosimetric Predictors of Prolonged Grade 2 Urinary Symptoms After Prostate Implantation: What Does The Urethral DVH Teach Us?", to be presented at the Annual American Brachytherapy Society Meeting New York 2003.

Juanita Crook, M.D. et al., "Factors Influencing Risk of Acute Urinary Retention After Trus–Guided Permanent Prostate Seed Implantation", Int. J. Radiation Oncology Biol. Phys., vol. 52, No. 2, pp. 453–460, 2002 Copyright © 2002 Elsevier Science Inc.

Gregory S. Merrick et al., "Prophylactic Versus Therapeutic Alpha–Blockers After Permanent Prostate Brachytherapy", Urology 60 (4), 2002, pp. 650–655.

(List continued on next page.)

*Primary Examiner*—Ali Imam
(74) *Attorney, Agent, or Firm*—Malloy & Malloy, PA

(57) ABSTRACT

A method of identifying a patient's urethral anatomic course for the precise placement of a treatment element into the patient's prostate, wherein a catheter containing an imaging bladder is introduced into a urethra until it is generally aligned with a treatment site of the prostate. An imaging probe is positioned relative to the treatment site and the urethra and is activated to obtain a real time image of the treatment site. The bladder is filled to define an acoustic interface between its interior and the urethral wall. A boundary of the urethra is identified at the acoustic interface during placement of the treatment element to position it relative to the urethra. A urethral identification system includes a catheter having the bladder spaced from the tip thereof and inflated allowing the bladder to contact the urethral wall and define the acoustic interface that is visible utilizing an ultrasound imaging device.

53 Claims, 4 Drawing Sheets

OTHER PUBLICATIONS

Michael J. Zelefsky, M.D., et al, "Postimplantation Dosimetric Analysis of Permanent Transperineal Prostate Implantation: Improved Dose Distributions With An Intraoperative Computer–Optimized Conformal Planning Technique", Int. J. Radiation Oncology Biol. Phys., vol. 48, No. 2, pp. 601–608, 2000 Copyright © 2000 Elsevier Science Inc., PII S0360–3016 (00) 00655–6.

Michael J. Zelefsky, M.D., et al., "The Role of Brachytherapy in the Management of Clinically Localized Prostate Cancer", 2000, *Pro Updates Principles & Practice Of Oncology*, vol. 14, No. 11, pp. 1–12.

Ernest H. Agatstein, MD., FACS, "Water–Induced Thermotherapy (WIT™) : A True Office–Based Procedure for BPH", *PROTRENDS*, pp. 2–3.

* cited by examiner

URETHRAL IDENTIFICATION SYSTEM AND METHOD OF IDENTIFYING A PATIENT'S URETHRAL ANATOMIC COURSE IN REAL TIME FOR THE PRECISE PLACEMENT OF A PROSTATE TREATMENT ELEMENT

CLAIM OF PRIORITY

The present application is based on and a claim to priority is made under 35 U.S.C. Section 119(e) to provisional patent application currently now abandoned in the U.S. Patent and Trademark Office having Ser. No. 60/469,213 and a filing date of May 10, 2003.

BACKGROUND OF THE INVENTION

1. Field of the Invention

The present invention relates to a method of identifying a patient's urethral anatomic course which is especially suited for accurately locating a brachytherapy or cryoablation treatment element into a patient's prostate thereby allowing a practitioner to achieve optimal spacing between the treatment element and the urethra, while still effectively positioning the treatment element in effective and operative proximity to a tumor, Benign Prostatic Hyperplasia (BPH) tissue, or other desired treatment site within the prostate. In this regard, the present invention is further directed towards a urethral identification system and more specifically a urethral identification catheter which substantially enhances the identifyability of the urethral boundary at the prostate by generating, on demand, an acoustic interface that is effectively visible utilizing ultrasound equipment. As a result, utilizing the present system and method, a practitioner can take into account the possible detrimental effects of locating treatment elements, such as radioactive seeds and/or cryo-probes, too close to the urethra itself, while still appropriately positioning the treatment element to effectively treat or affect a tumor, BPH tissue or other treatment site.

2. Description of the Related Art

The prostate is a male accessory sex organ located inferior to the urinary bladder and anterior to the rectum. Roughly the size of a walnut, the prostate is located in generally close proximity to the urinary bladder and surrounds and/or encircles an upper part of the urethra, the tube that is connected to the urinary bladder and empties urine therefrom. Prostate cancer is potentially aggressive and is the second leading cause of cancer deaths among men in the United States. When diagnosed at an early, localized stage and when the disease is organ confined, prostate cancer is also often considered one of the most treatable and curable forms of cancer. As a result, early detection and effective treatment is of a critical nature.

Over the years a variety of different techniques and procedures have been developed in an effort to effectively treat prostate cancer, as well as other disorders associated with the prostate, including, but not limited to Benign Prostatic Hyperplasia (BPH). Specifically, in addition to traditional radiation/chemotherapy treatments which are commonly employed for a variety of different types of cancer, due to the localized nature of prostate cancer, if detected sufficiently early, a variety of additional techniques to treat prostate tumors have been developed.

Of the existing treatments, one procedure involves the complete removal of the prostate from the patient and/or the resection of affected portions of the prostate. Given the nature of a malignant tumor, when surgery is the elected course of treatment, complete removal of the prostate is generally undertaken. However, in many circumstances surgery for the removal of a prostate may not be desirable for a variety of reasons. Among these are the post operative risks of urinary incontinence and erectile dysfunction, and co-morbid medical conditions which may increase a patient's morbidity and/or intra-operative mortality. The anatomic location of the prostate, in relation to the external urinary sphincter and the lateral neurovascular bundles, mandates that extirpative surgical procedures for the prostate, maintain the integrity of the external urinary sphincter and preserve the neural erectile pathways. Therefore, it may be preferable to leave the prostate intact. As a result, alternative minimally invasive techniques which treat prostatic malignancies, but do not require removal of the prostate may ultimately be the preferred course of treatment, and such treatment protocols are continuously being perfected.

In particular, there exist a variety of novel techniques which do not require a patient to be subjected to excessive doses of radiation, but which perform substantially localized treatment directly to the prostate. One such technique known as transperinael interstitial brachytherapy ("brachytherapy") is commonly utilized when managing localized prostate cancer. Specifically, brachytherapy involves the trans-perineal delivery of radioactive implants, sometimes referred to as seeds, into the stroma of the prostate and in substantially close proximity to the tumor, for an extended period of time. In this regard, the one or more radioactive seeds can directly and/or locally treat a malignant tumor, often ultimately destroying the tumor, with limited effects to the rest of the patient's body.

Still another technique of localized treatment of a malignant tumor in the prostate, as well as the treatment of BPH, a condition whereby prostatic hypertrophy can result in an impediment to the evacuation of urine through the urethra, involve a treatment method known as cryoablation of the prostate. Under such cryoablation techniques, one or more cryo-probes and temperature sensing probes are introduced into the prostate into operative proximity with the malignant tumor or the desired treatment site. Specifically, the cryo-probes often include small gauge needles that can be effectively inserted into the prostate from the exterior of the patient. Through these cryo-probes, a cold temperature is effectively delivered at the treatment site, such as the site of the tumor, such as through the delivery of a cryogen gas including argon gas. Once the cryogen is delivered, a field of cold temperature is generated that forms essentially an ice ball to contain a majority of the lethal portions of the tumor, and/or to shrink the prostate. Subsequently, these ice balls are allowed to thaw, and then one or more subsequent freeze/thaw cycles can be performed in an effort to effectively cure the malignancy of the tumor and/or relieve the pressure resulting from the BPH.

In addition to the above techniques for localized treatment of a tumor and/or BPH and/or other aliments of the prostate, it is also recognized that other techniques are continuously being developed, refined and/or tested in an effort to achieve directed and localized treatment of tumors or other disorders within the prostate. Generally in such techniques, and especially in the techniques of brachytherapy and cryoablation, it is of significant importance for a practitioner to obtain an effective image of the prostate in order to identify a deposit location of the treatment element, be it radioactive seeds and/or cryo-probes, without performing highly invasive procedures. Traditionally, such imaging of the prostate is achieved utilizing transrectal ultrasonography.

In particular, transrectal ultrasonography requires that a practitioner insert an ultrasound probe into the rectum, and utilizing the probe, direct ultrasound towards the prostate. When employing such an ultrasound system, the practitioner is thereby able to visualize an image of the prostate, on a monitor, in real time during the positioning of a treatment element. Unfortunately, while such techniques are generally effective for viewing the exterior shape and location of the walnut sized prostate; due to the inherent physical nature of the prostate and its circumferential orientation around the proximal urethra, practitioners typically cannot obtain any meaningful, sustained, and standardized imaging of the urethra, and more specifically the anatomic course of the prostatic urethra. There currently exist some techniques for achieving a fleeting and inconsistent viewing of the urethra. Such techniques include the manual manipulation of a Foley catheter within the urethra or the introduction of an aerated gel into the catheter. Such techniques, however, cannot be readily controlled into a standardized and manageable on and off position, and generally provide merely a temporary, variable glimpse of the urethra, if any. Furthermore, based upon the previous, traditionally accepted practice, it was not necessary for the practitioner to be able to view and/or recognize the urethral boundaries within the prostate, as the primary item of importance related to appropriate viewing of the shape, size and location of the prostate so as to effectively achieve proper positioning of the treatment element within the prostate. Also, given the general desire to minimize the potential negative impact of the treatment elements, and especially the radioactivity from the radioactive seeds on the surrounding tissue and/or organs, the treatment elements have traditionally been implanted substantially into the prostate, such that the prostate itself would act as a shield for the external tissues and/or organs.

Although such practices had been traditionally accepted, more recent studies in brachytherapy have concluded that positioning of a treatment element in substantially close proximity to the urethra, such that the urethra is exposed to higher radiation doses, can correlate with urethral toxicity. The subsequent detrimental effects to the urethra may be clinically experienced as irritative voiding symptoms, urinary retention, and/or recto-urethral fistulas. Therefore, determining the precise location for the placement of the treatment element, such as radioactive seeds, relative to the urethra, can impact the nature, location, and quantity of treatment to be employed. As a result of these discoveries, it would be highly beneficial to provide a method and system which can effectively provide for the identification of the urethral course through the prostate, thereby allowing a practitioner, in real time, to effectively identify not only the external boundaries of the prostate, but also the urethral boundary, thereby taking both boundaries into consideration when appropriately positioning a treatment element, such as radioactive seeds and/or cryo-probes. In particular, ideal techniques may call for a positioning of the treatment element in substantially close proximity to a malignant tumor, while maintaining a maximum possible spacing from the urethral boundary. As indicated, however, presently available systems and methods do not permit for the effective viewing and/or distinguishing of the urethra relative to the prostate so as to substantially aid in treatment, and no identification systems and/or techniques which provide for a clearly visible, on demand on/off, and standardized visualization are known to be implemented. As a result, the method and system of the present invention can provide a substantial enhancement in the field of art associated with localized treatment of tumors and other disorders, such as BPH, within the prostate in a manner which reduce urethral exposure to the treatment element and thereby reduce post operative complications to the urethra.

SUMMARY OF THE INVENTION

The present invention relates to a system and method of identifying a patient's urethral anatomic course in real time, and especially at the location of the prostate, in order to facilitate the precise placement of a treatment element within the prostate in a desired location relative to the urethral boundary. In particular, the present urethral identification system may include a urethral identification catheter. This identification catheter includes an elongate catheter with a primary lumen and a tip structured to be inserted into a patient's urethra into fluid flow communication with a urinary bladder of the patient. Further, the elongate catheter will preferably have a sufficient length such that a tip of the catheter will actually extend into the urinary bladder of the patient, and in a preferred embodiment, a tip bladder is provided generally at the tip of the elongate catheter. The tip bladder is structured to be inflated, once introduced into the urinary bladder of the patient, so as to effectively resist removal of the catheter from the urinary bladder and urethra.

Additionally, the urethral identification catheter of the urethral identification system also includes an imaging bladder. The imaging bladder is at least partially, but preferably completely disposed about the elongate catheter in spaced relation from a tip of the catheter. Preferably, the spaced relation from the tip of the catheter will be a distance which appropriately positions the imaging bladder within the portion of the urethra which is surrounded by a prostate of the patient. Furthermore, connected in fluid flow communication with the imaging bladder is an inflation conduit. The inflation conduit is structured to direct a fluid, and preferably a gas such as air, into the imaging bladder. The air, which is preferably introduced into the imaging bladder once the imaging bladder has been appropriately positioned in a desired location within the urethra, causes the imaging bladder to be inflated and to engage, at least somewhat, and substantially conform to at least a portion of the urethral wall. Also, in a preferred embodiment, the imaging bladder has a substantially thin walled construction so as to minimally interfere with imaging, as will be described.

Further provided as a part of the urethral identification system is an imaging device. Preferably, the imaging device includes an ultrasound type device with an imaging probe that is disposed in operative proximity to the imaging bladder and generally the prostate and urethra of the patient. Preferably through the use of the imaging probe, the imaging device is structured to provide a real time image of a vicinity of the imaging probe and is structured to effectively view and identify an acoustic interface that is defined between the fluid disposed in the imaging bladder and the urethral wall. This acoustic interface is substantially visible utilizing the imaging device and based upon the inflation of the imaging bladder and its close proximity with the wall of the urethra effectively identifying a boundary of the urethra at the air/liquid interface therebetween. As a result, a practitioner is effectively able to identify the urethral boundary and/or the wall of the urethra, as well as being able to view the prostate both before and during introduction of the treatment element. Moreover, the practitioner has substantial control over the viewing process since inflation and/or deflation of the image bladder can provide an on demand, on/off type imaging that can generate a meaningful, manageable and standardized display for an extended period of time as needed by the practitioner.

From the preceding, it is seen that the present urethral identification system and urethral catheter may be the preferred implements to be utilized within a method of identifying a patient's urethral anatomic course, in real time for the precise placement of a treatment element into the patient's prostate. In particular, the method preferably includes an initial step of inserting a catheter that contains an external inflatable imaging bladder into the urethra of the patient until the imaging bladder is generally aligned with a treatment site of the prostate. Additionally, an imaging probe is operatively positioned relative to the treatment site of the prostate and proximate portions of the urethra. This imaging device, will ultimately be activated so as to obtain a real time image of the treatment site of the prostate, such as on an associated monitor which may be viewed by a practitioner.

With the imaging bladder appropriately positioned within the urethra of the patient, the imaging bladder is inflated, preferably by a fluid such as air, until the imaging bladder engages the urethral wall and an acoustic interface is defined between the interior of the imaging bladder and the urethral wall. In this regard, it is noted that this engagement may include a close spacing therebetween so long as effective definition of the urethral wall within the required degree of certainty for the procedure can be achieved. As a result, a boundary of the urethra at that acoustic interface can be thereafter identified during placement of the treatment element, and proper positioning of the treatment element relative to the urethra can be ensured.

These and other features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
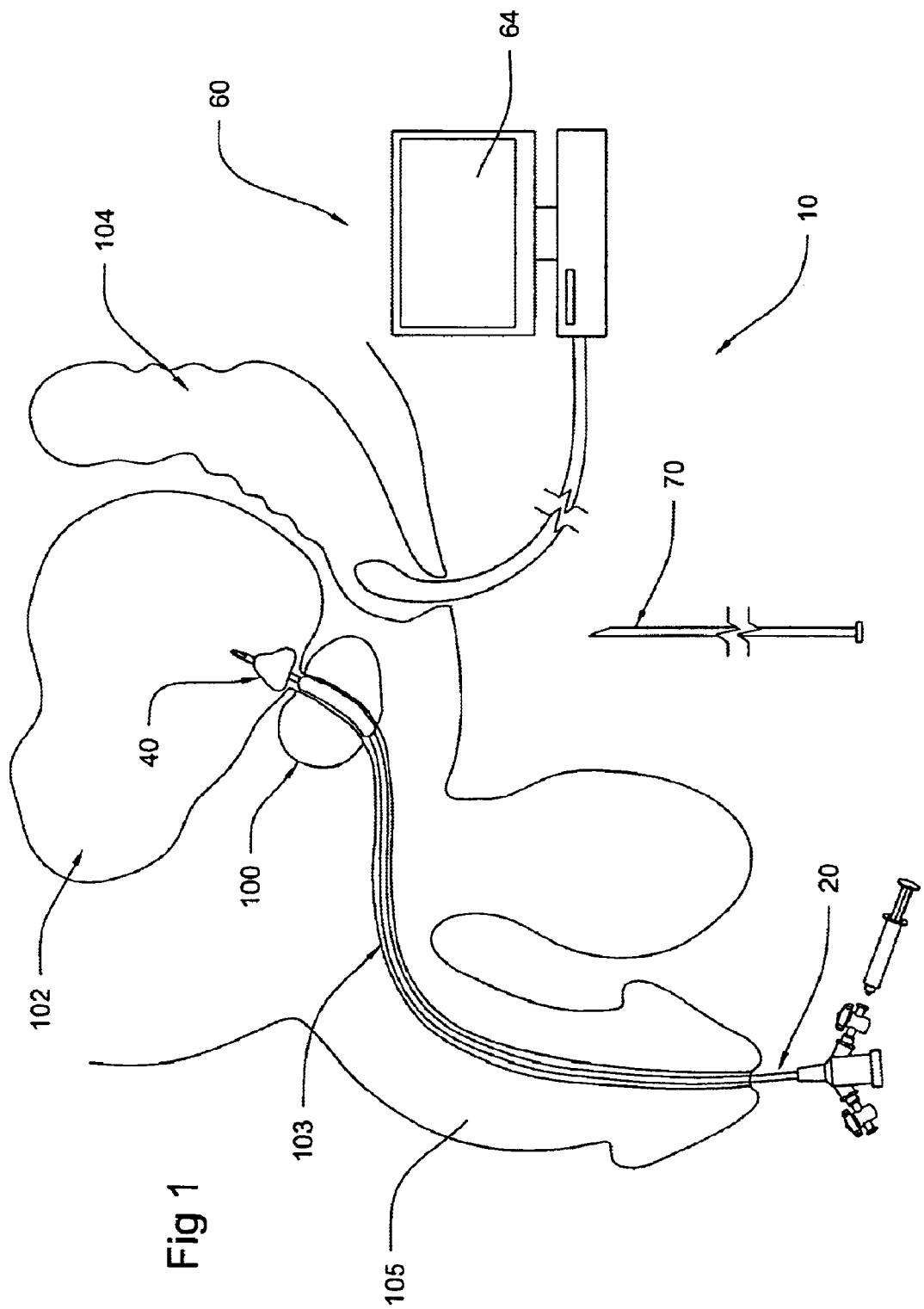
FIG. 1 is a detailed schematic illustration of the urethral identification system of the present invention operatively disposed relative to a patient.
Figure 2:
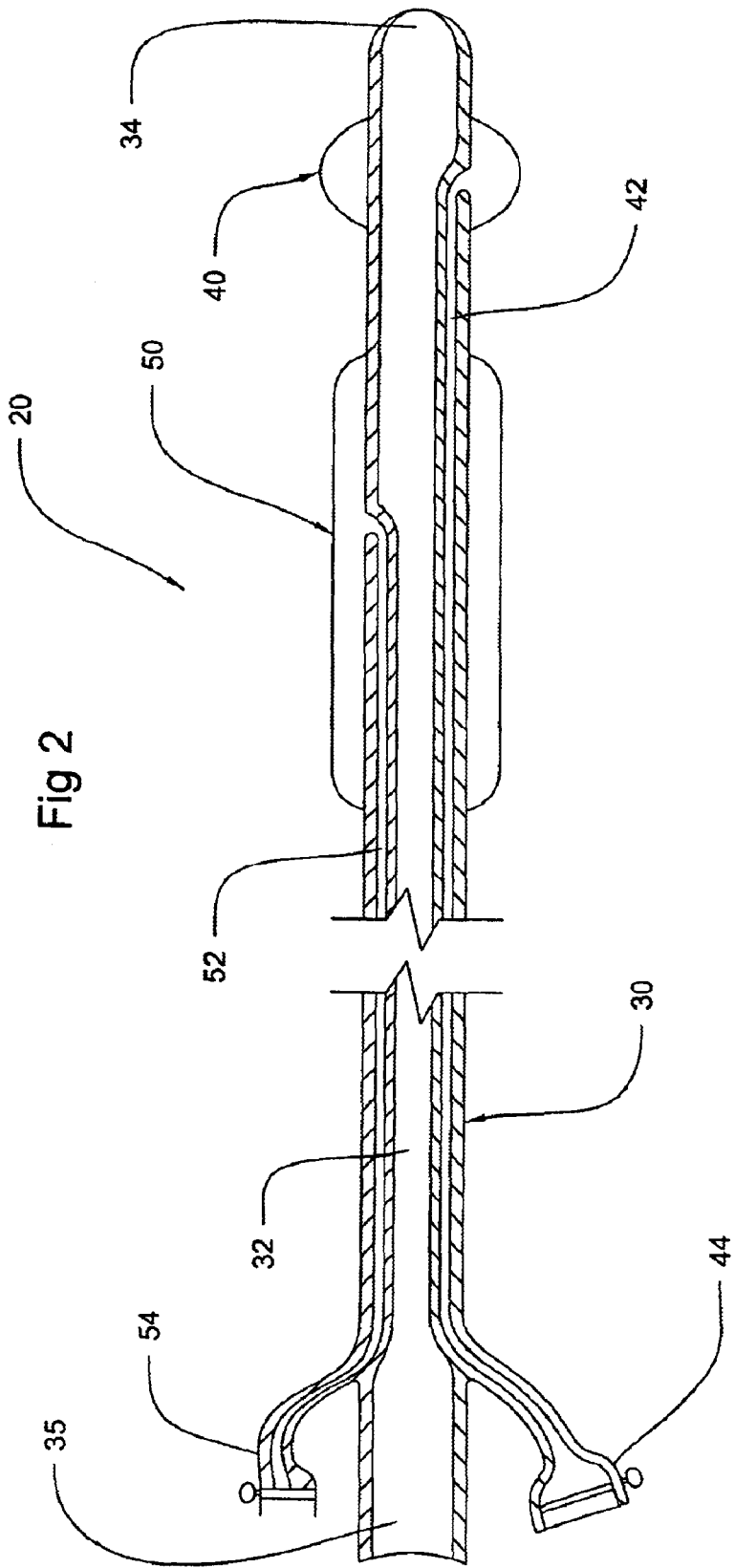
FIG. 2 is a partial cross section view of one embodiment of the urethral identification catheter of the present invention.
Figure 3:
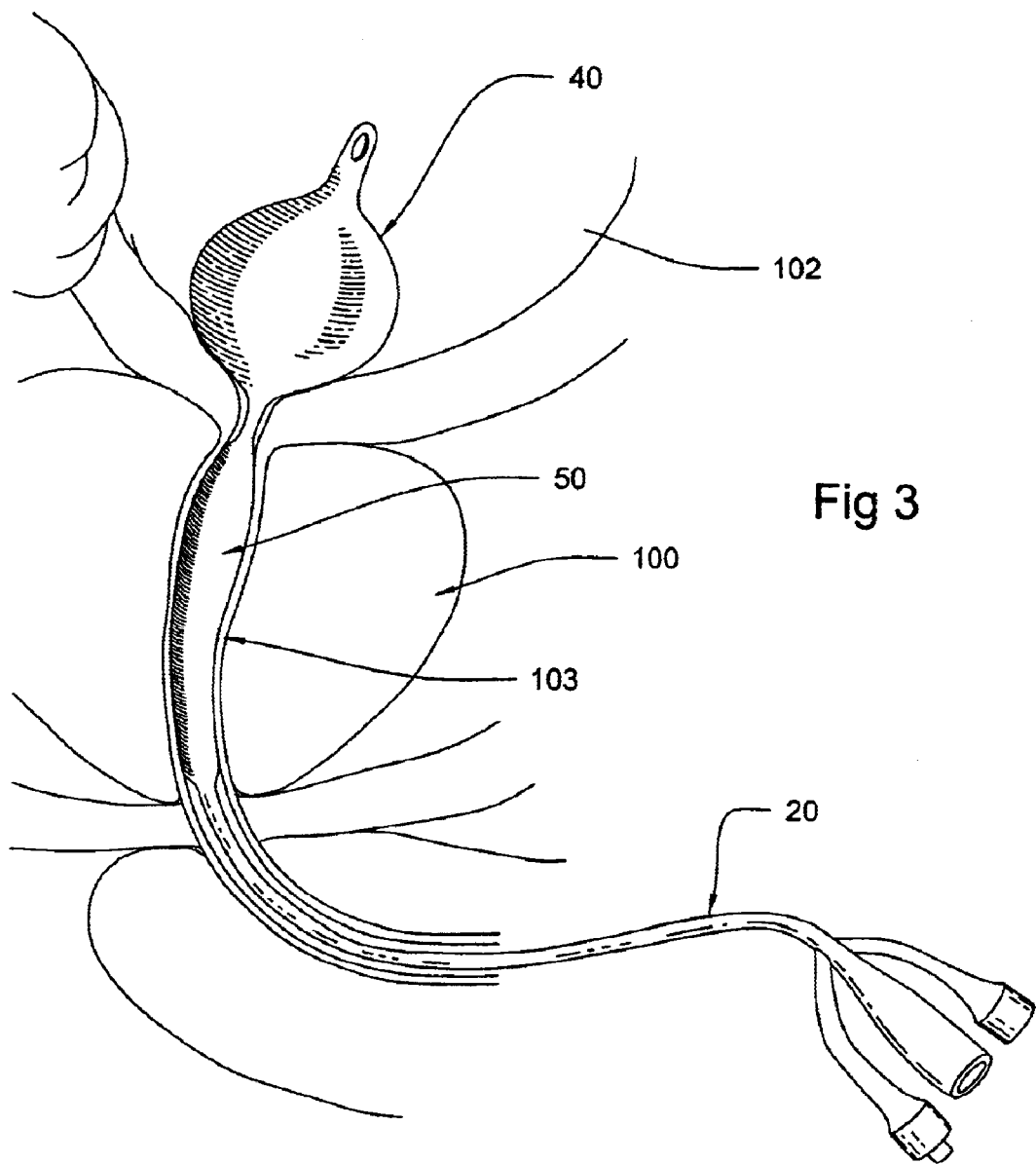
FIG. 3 is an operative view of one embodiment of the urethral identification catheter of the present invention.

The present invention is directed towards a urethral identification system, generally indicated as 10, and further to a method of identifying a patient's urethral anatomical course, in real time in order to aide in the precise placement of a treatment element into the patient's prostate 100. Also, as will be described in greater detail subsequently, the preferred method of the present invention relates to the effective placement of a brachytherapy radioactive seed and/or a cryoablation cryo-probe, with precision, at a desired location within the patent's prostate 100.

Looking first to the illustrated embodiments of the urethral identification system 10, it includes a urethral identification catheter, generally 20. In particular, the urethral identification catheter 20 includes an elongate catheter, similar in length to that of a traditional use Foley catheter. The elongate urethral identification catheter 20 is structured to be introduced into the urethra 103 of a patient through the penis 105 until a proximate tip 34 thereof extends into a urinary bladder 102 of the patient so as to drain urine from the urinary bladder 102. Furthermore, the elongate urethral identification catheter 20 also includes a primary lumen 32 that extends generally from the tip 34 that is inserted into the patient's urinary bladder 102 to an exterior, open end 35. In this manner, and through this primary lumen 32, urine may be drained from the patient's urinary bladder 102 during the performance of this and other procedures as necessary, and/or after the procedure. Further provided in a preferred embodiment of the urethral identification catheter 20 is a tip bladder 40. In particular, the tip bladder 40 is formed of a flexible balloon type material and is structured to be effectively expanded upon the introduction of a fluid therein. In order to aid the inflation of the tip bladder 40, a secondary lumen 42 is provided in fluid flow communication between the tip bladder 40 and an inlet port 44. The inlet port 44 may include any desirable valve construction so as to effectively allow for the introduction of a fluid while regulating the escape of a fluid. In use, the elongate urethral identification catheter 20 is introduced into the patient's urethra 103 until the tip bladder 40 extends into the urinary bladder 102 of the patient. Once inserted into the urinary bladder 102 of the patient, the tip bladder 40 may thereafter be effectively inflated through the secondary lumen 42. By inflating the tip bladder 40, and as illustrated in the figures, the urethral identification catheter 20 is essentially maintained in its operative and fluid flow connection with the urinary bladder 102 of the patient. Specifically, the larger size of the tip bladder 40 relative to the opening to the urethra 103 from the urinary bladder 102 is such that removal of the catheter 20 is generally resisted. Furthermore, it noted that although the tip bladder 40 is not a prerequisite for the urethral identification catheter 20 and urethral identification system 10 of the present invention, it may be preferred as it will provide a precise positioning of the urethral identification catheter 20 within the patient. For example, once the tip bladder 40 is inflated, the catheter can be carefully pulled out from the urethra 103 until the tip bladder 40 engages the urinary bladder wall. As a result, a base of the tip bladder 40 will always be disposed at the entrance way to the urethra 103 from the urinary bladder 102.

Looking further to the preferred urethral identification catheter 20, it also preferably includes an imaging bladder 50. In particular, the imaging bladder 50 is at least partially, and preferably completely, disposed about an exterior surface of the catheter, although it is recognized that internal placement with appropriate open or flexible construction of the catheter wall can also be achieved. Further, the imaging bladder 50 may be completely cylindrical, helical, fluted, cone shaped or another symmetrical or non-symmetrical shape. A further auxiliary lumen or inflation conduit 52 is also provided and is communicatively disposed between the imaging bladder 50 and an inlet port 54 that includes an appropriate flow control valve structure. As a result, in use, a fluid may be passed through this auxiliary lumen 52 into inflating position within the imaging bladder 50, such as using a proximately integrated inflation device or a separate device such as a syringe.

Looking to the preferred embodiments of the imaging bladder 50, it is preferably structured to be a low pressure bladder inflated by a fluid and preferably air, for reasons to be subsequently described. Furthermore, the imaging bladder 50 is preferably formed of a flexible material which may be made of latex or be latex-free material such as including silicone, polyurethane, polyethyleneteraphalete or another latex-free material, so as to allow for appropriate inflation thereof. The preferred material construction of the imaging bladder 50 is achieved so as to minimize the potential obstruction to be generated by the imaging bladder 50 to an imaging device 60, to be described in greater detail subsequently. Furthermore, to aide and/or minimize the obstruction of the imaging, to allow maximum conformance of the imaging bladder 50 to the urethral wall, if desired, and to provide a clearly visible indicator, the imaging bladder 50 will preferably be formed of a substantially thin wall thickness in the range of 0.0001 inches to 0.1 inches, and in the preferred, illustrated embodiments a wall thickness of between 0.001 to 0.005 inches. Further an inflated diameter of approximately 14 Fr (French)–30 Fr may be preferred, with a non-inflated dimension of between approximately 14 Fr–22 Fr may also be desirable. Specifically, and as will be described in greater detail subsequently, the imaging bladder 50 is structured to be inflated under low pressure only until it engages, at least partially, and exerts a mild outward pressure on the urethral wall. As a result, a thick wall, high volume/high pressure structure of the imaging bladder 50 is not required, and indeed in some embodiments may actually be detrimental due to its imaging obstruction. Furthermore, a thin wall thickness and flexible material provides a greater degree of conformity with the urethral wall, if so desired, so that a more accurate image is defined. Moreover, because the practitioner has substantial control over the inflation and/or deflation of the imaging bladder 50 in an on demand type system, the practitioner has substantial control over the viewing process as well, essentially being able to turn on optimized, continuous and manageable imaging of the urethral course, as needed, and until no longer needed.

As can be seen from the Figures, the imaging bladder 50 when operatively disposed with the urethral identification catheter 20 in the patients urethra is preferably aligned with at least a portion and in many embodiments all of the prostate 100. Specifically, the prostate which is the walnut sized sex organ that wraps around an upper portion of the urethra 103 substantially near the urinary bladder 102 typically has a somewhat standard range of dimensions, at least with regard to the length of the urethra 103 overlapped thereby. Moreover, through various imaging techniques a general determination of the length of the prostate 100 may be determined to select an appropriate sized imaging bladder. As a result, the imaging bladder 50 preferably extends through a substantial portion of the urethra 103 that is encased by the prostate 100, and, in the preferred embodiment the imaging bladder 50 is preferably about 4 cm in length. Of course, it is understood that varying lengths may also be provided if greater precision and/or larger coverage area is desired.

Also, the imaging bladder 50 is preferably, although not necessarily, disposed a slightly spaced apart distance from the tip bladder 50 in order to be appropriately positioned relative to the prostate 100. In the illustrated embodiment, the imaging bladder 50 may be closely spaced from the base of the tip bladder 40, that spacing generally positioning the imaging bladder 50 in an appropriately aligned position relative to the prostate 100 when the tip bladder 40 has been inflated and is engaging the walls of the urinary bladder 102.

Further provided as part of the urethral identification system 10 of the present invention is an imaging device, generally 60. Although the imaging device 60 may include any of a number of different types of imaging devices which provide an accurate, real time view of internal organs, including yet to be developed imaging devices, in the preferred, illustrated embodiments the imaging device 60 includes an ultrasound type system. In this regard, an imaging probe 62 is preferably provided and is structured to emit sound waves in a conventional fashion towards the prostate so as to generate ultrasound images on an associated monitor 64 and processor assembly. In use, the imaging probe 62 is preferably inserted into the rectum 104 of the patient as that provides a substantially close proximity to the prostate 100, and as a result, to the imaging bladder 50 that is located within the prostate 100.

As previously recited, the imaging bladder 50 is preferably inflated with a fluid, and preferably air, through any conventional means such as through the utilization of a syringe at the inlet port 54 or a proximately integrated inflation/deflation device. With the imaging bladder 50 generally inflated such that it at least partially and preferably substantially contacts, conforms to and engages the urethral wall, an effective image can be achieved by the imaging device 60. In particular, it is noted that although the urethra 103 is generally not visible and/or readily discernable within the prostate 100 utilizing ultrasound and/or other standard imaging techniques, by inflating the imaging bladder 50 with air, an acoustic interface that is clearly visible utilizing the imaging device 60 is generated and defined. Specifically, the contrast between the fluid disposed within the imaging bladder 50 and the urethral wall defines the acoustic interface, thus allowing a practitioner utilizing the image device 60 to readily view, on their monitor 64, a boundary of the urethra as the contrast point. This boundary of the urethra 103 may then be monitored during performance of a necessary procedure, such as the effective location of a treatment element 70 in the prostate 100. In this regard, it is also noted that the fluid utilized to inflate the imaging bladder may include a radio-opaque material or other contrast medium that can be viewed using ancillary imaging modalities including fluoroscopy as the imaging device, and/or if desired, the imaging bladder may be pre-inflated partially and/or completely.

As previously recited, in the preferred embodiment the treatment element 70 may include a brachytherapy probe that introduces one or more radioactive seeds into the prostate 100 of the patient. Alternatively, the treatment element 70 may include one or more cryo-probes and/or temperature sensing probes that are inserted into the prostate 100 of the patient in order to achieve effective cryoablation of a tumor that may be contained within the prostate 100 or treatment for BPH. In either such instances, however, effective positioning of the treatment element 70 within the prostate 100, taking into account a desired optimal spacing with the urethral wall can be achieved. Moreover, such placement may also impact the nature and/or extent of treatment, such by helping in the determination of the number of radioactive seeds to be used and/or the determination of the progress of BPH treatment.

Figure 4:
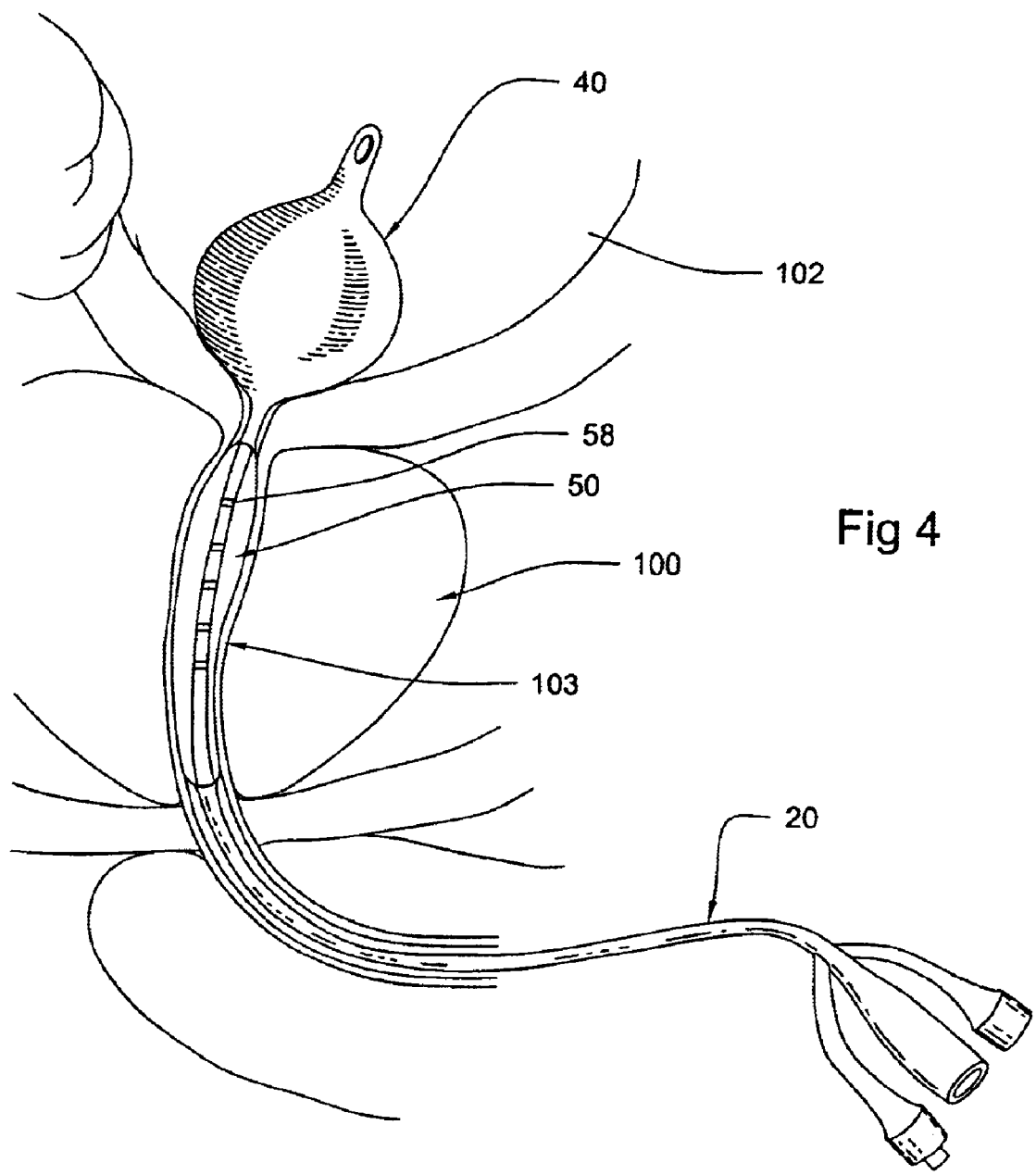
FIG. 4 is an operative view of an alternative embodiment of the urethral identification catheter of the present invention.

Looking to FIG. 4, in an alternative embodiment of the urethral identification catheter 20 of the present invention, in addition to the imaging bladder 50, it is also seen that one or more hyperechoic rings 58 may also be provided and disposed completely or partially around a periphery of the catheter. These hyperechoic rings 58 may be defined on an exterior of the catheter, such as using an echogenic coating on or in the surface material of the catheter, as may be desired. Specifically, the hyperechoic rings 58 will exhibit visible landmark images when utilizing the imaging device 60, those landmarks also being potentially helpful for the selection of a treatment element 70 and/or the effective and appropriate positioning of a treatment element 70, as needed. In the illustrated embodiment, the hyperechoic rings 58 are preferably formed of an echogenic material and spaced 1 cm from one another. Of course, it is understood that other hyperechoic materials and/or varied spacing and/or numbering of the hyperechoic rings 58 may also be employed if the hyperechoic rings 58 are ultimately utilized in the urethral imaging catheter 20.

Utilizing, the preceding urethral identification system 10 and the urethral identification catheter 20, it is further seen that the present direction may be directed towards a method of identifying a patient's urethral anatomic course, in real time, for the precise placement of a treatment element 70 into the patient's prostate 100. In use, the present method may include an initial step of introducing a catheter that has at least an external imaging bladder 50, and in some preferred embodiments a tip bladder 40 into the urethra 103 of the patient until the image bladder 50 is generally aligned with a treatment site of the prostate 100, and in some embodiments until the tip bladder 40 is disposed within the urinary bladder 102. When appropriate, the tip bladder 40 may be effectively inflated thereby securing the catheter within the urethra 103 of the patient. Furthermore, also when appropriate, the imaging bladder 50 is preferably inflated, preferably utilizing a fluid such as air, and preferably until the exterior wall of the imaging bladder 50 generally abuts and/or engages at least a portion of the urethral wall at the prostate 100. In this regard, it may be preferred that the imaging bladder 50, which as previously recited may have a substantially thin wall thickness, will generally conform to the anatomic course of the urethra 103 and will only exert a mild pressure on the urethra 103, although minimal contact is also possible.

The present method further includes the step of placing an imaging probe 62 in operative proximity to the imaging bladder 50, and generally in operative proximity to the prostate 100 that is preferably aligned therewith. This step in the method preferably includes the insertion of an ultrasound probe 62 into the rectum 104 of the patient, and ultimately activating the imaging device 60 so as to produce a real time image of the prostate 100 of the patient. Additionally, it is noted that either prior to or subsequent to the activation of the imaging device 60, the imaging bladder 50 is filled with the fluid such as air. The imaging bladder 50 is filled until an acoustic interface is defined between the interior of the imaging bladder 50 and the urethral wall, this acoustic interface being achieved generally when a sufficient pocket of air is defined next to the urethral wall. A practitioner may then, preferably utilizing the imaging device 60 appropriately identify and view a boundary of the urethra 103 at the acoustic interface, and effective placement of a treatment element 70 can thereafter proceed. Indeed, it is this flexibility of activation/inflation that gives the practitioner substantial control over the imaging process. For example, by achieving inflation and/or deflation of the imaging bladder 50 in an on demand type system, the practitioner has substantial control and can turn on an optimized, continuous image of the urethral course as needed and until no longer needed. Moreover, the process can be generally standardized from one case to another.

In one embodiment of the present method the effective placement of the treatment element 70 comprises the insertion of one or more elongate brachytherapy probes which allow for the positioning of radioactive seeds in operative proximity to a tumor located within the prostate 100. Utilizing the image that is identified and viewed utilizing the imaging device 60, appropriate relative positioning of the radioactive seeds between the exterior of the prostate 100, the urethral boundary and the tumor to be treated can appropriately be achieved. Further, in an alternative embodiment of the present method the treatment element 70 may include one or more cryoablation cryo-probes, as well as potentially one or more temperature sensing probes. In use, the temperature sensing probes and/or cryo-probes are introduced into the prostate 100 in effective operative proximity to a tumor or other treatment site within the prostate 100. As previously recited, this appropriate spacing utilizing the imaging of the urethral boundary can take into account both the urethral boundary and the exterior of the prostate 100. Once the one or more cryoablation probes are effectively positioned a series of freezing and thawing cycles may then take place, such as through the introduction of a cryogenic gas, like argon gas, to create an ice ball at the tumor located within the prostate 100 and/or to treat the BPH. As a result, in either such embodiment and/or in any other embodiment wherein a treatment element, such as a microwave or other heating element to treat BPH or another ailment associated with the prostate, must be effectively placed within the prostate 100, a practitioner need not unduly sacrifice the health and integrity of the urethra 103 in positioning a treatment element 70, but rather can now take into account the appropriate location, size and orientation of the urethra 103 within the prostate 100 when determining an ideal location for a treatment element 70.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents, and may extend to alternate imaging needs outside of the prostate context.

Now that the invention has been described,

What is claimed is:

1. A method of identifying a patient's urethral anatomic course in real time for the precise placement of a treatment element into the patient's prostate, said method comprising:
   a) introducing a catheter containing an external imaging bladder into a urethra of the patient until said image bladder is generally aligned with a treatment site of the prostate;
   b) operatively positioning an imaging probe of an imaging device relative to the treatment site of the prostate and proximate portions of said urethra;
   c) activating said imaging device so as to obtain a real time image of the treatment site of the prostate;
   d) filling said imaging bladder on demand until said imaging bladder defines an acoustic interface between the interior of said imaging bladder and the urethral wall; and
   e) identifying and viewing a boundary of said urethra at said acoustic interface during placement of said treatment element so as to identify proper positioning thereof relative to the urethra.

2. The method of claim 1 further comprising:
   a) introducing said catheter containing a tip bladder and said external, inflatable imaging bladder positioned a determined spacing therefrom into the urethra of the patient until said tip bladder enters the patient's urinary bladder;
   b) inflating said tip bladder so as to prevent removal thereof from the patient's urinary bladder; and
   c) withdrawing said catheter from the patient's urethra until said tip bladder engages the patient's urinary bladder in proximity to an entrance to said urethra so as to position said image bladder in generally aligned relation with the treatment site of the prostate.

3. The method of claim 1 further comprising inflating said imaging bladder with a fluid.

4. The method of claim 3 further comprising inflating said imaging bladder with air.

5. The method of claim 1 further comprising at least partially filling said imaging bladder with a radio-opaque material.

6. The method of claim 1 further comprising operatively positioning a transrectal ultrasonography probe into a rectum of the patient until said probe is in imaging proximity to the patient's prostate.

7. The method of claim 1 further comprising inflating said imaging bladder until said imaging bladder begins to contact and minimally expand the urethral wall.

8. The method of claim 1 further comprising introducing said catheter having said imaging bladder formed of a substantially thin walled construction.

9. The method of claim 1 further comprising introducing said catheter having said imaging bladder with a wall thickness of approximately 0.0001 inches to 0.1 inches.

10. The method of claim 1 further comprising introducing said catheter having said imaging bladder with a wall thickness of approximately 0.001 inches to 0.005 inches.

11. The method of claim 1 further comprising introducing said catheter having said imaging bladder with a filled diameter of approximately 14 Fr–30 Fr.

12. The method of claim 1 further comprising introducing said catheter having said imaging bladder formed of a latex free material.

13. The method of claim 1 further comprising introducing said catheter having said imaging bladder formed of a latex material.

14. A method of precisely locating a brachytherapy treatment element into a patient's prostate, said method comprising:
 a) introducing a catheter containing an external, inflatable imaging bladder into a urethra of the patient until said image bladder is generally aligned with a treatment site of the prostate;
 b) operatively positioning an imaging probe of an imaging device relative to the treatment site of the prostate and proximate portions of said urethra;
 c) activating said imaging device so as to obtain a real time image of the treatment site of the prostate;
 d) filling said imaging bladder on demand until said imaging bladder engages the urethral wall and an acoustic interface is defined between the interior of said imaging bladder and the urethral wall;
 e) identifying and viewing a boundary of said urethra at said acoustic interface; and
 f) introducing the brachytherapy treatment element into the prostate within a vicinity of a tumor and at a determined spacing from the boundary of said urethra so as to minimize adverse affects on the urethra.

15. The method of claim 14 further comprising inflating said imaging bladder with air.

16. The method of claim 14 further comprising:
 a) introducing said catheter containing a tip bladder and said external, inflatable imaging bladder positioned a determined spacing therefrom into the urethra of the patient until said tip bladder enters the patient's urinary bladder;
 b) inflating said tip bladder so as to prevent removal thereof from the patient's urinary bladder; and c) withdrawing said catheter from the patient's urethra until said tip bladder engages the patient's urinary bladder in proximity to an entrance to said urethra so as to position said image bladder in generally aligned relation with the treatment site of the prostate.

17. The method of claim 14 further comprising operatively positioning a transrectal ultrasonography probe into a rectum of the patient until said probe is in imaging proximity to the patient's prostate.

18. The method of claim 14 further comprising introducing said catheter having said imaging bladder with a wall thickness of approximately 0.0001 inches to 0.1 inches.

19. The method of claim 14 further comprising introducing said catheter having said imaging bladder with a wall thickness of approximately 0.001 inches to 0.005 inches.

20. The method of claim 14 further comprising introducing said catheter having said imaging bladder with an inflated diameter of approximately 14 Fr to 30 Fr.

21. The method of claim 14 further comprising introducing said catheter having said imaging bladder formed of a latex free material.

22. The method of claim 14 further comprising introducing said catheter having said imaging bladder formed of a latex material.

23. The method of claim 14 further comprising introducing a radioactive seed as the brachytherapy treatment element into the prostate.

24. The method of claim 23 further comprising introducing a plurality of said radioactive seeds as the brachytherapy treatment element into the prostate.

25. A method of precisely locating a cryoablation treatment element into a patient's prostate, said method comprising:
 a) introducing a catheter containing an external, inflatable imaging bladder into a urethra of the patient until said image bladder is generally aligned with a treatment site of the prostate;
 b) operatively positioning an imaging probe of an imaging device relative to the treatment site of the prostate and proximate portions of said urethra;
 c) activating said imaging device so as to obtain a real time image of the treatment site of the prostate;
 d) inflating said imaging bladder on demand until said imaging bladder engages the urethral wall and an acoustic interface is defined between the interior of said imaging bladder and the urethral wall;
 e) identifying and viewing a boundary of said urethra at said acoustic interface; and
 f) introducing the cryoablation treatment element into the prostate at a determined spacing from the boundary of said urethra so as to minimize adverse affects on the urethra.

26. The method of claim 25 further comprising introducing at least one cryoablation probe structured to freeze a portion of the prostate in a vicinity thereof.

27. The method of claim 26 further comprising introducing a plurality of said cryoablation probes.

28. The method of claim 25 further comprising inflating said imaging bladder with air.

29. The method of claim 25 further comprising inflating said imaging bladder with a radio-opaque material.

30. The method of claim 25 further comprising:
 a) introducing said catheter containing a tip bladder and said external, inflatable imaging bladder positioned a determined spacing therefrom into the urethra of the patient until said tip bladder enters the patient's urinary bladder;

b) inflating said tip bladder so as to prevent removal thereof from the patient's urinary bladder; and c) withdrawing said catheter from the patient's urethra until said tip bladder engages the patient's urinary bladder in proximity to an entrance to said urethra so as to position said image bladder in generally aligned relation with the treatment site of the prostate.

31. The method of claim 25 further comprising operatively positioning a transrectal ultrasonography probe into a rectum of the patient until said probe is in imaging proximity to the patient's prostate.

32. The method of claim 25 further comprising introducing said catheter having said imaging bladder with a wall thickness of approximately 0.0001 inches to 0.1 inches.

33. The method of claim 25 further comprising introducing said catheter having said imaging bladder with a wall thickness of approximately 0.001 inches to 0.005 inches.

34. The method of claim 25 further comprising introducing said catheter having said imaging bladder with an inflated diameter of approximately 14 Fr–30 Fr.

35. The method of claim 25 further comprising introducing said catheter having said imaging bladder formed of a latex free material.

36. The method of claim 25 further comprising introducing said catheter having said imaging bladder formed of a latex material.

37. A urethral identification system comprising:

a) an elongate catheter having a primary lumen and a tip structured to be inserted into a patient's urethra in fluid flow communication with a urinary bladder of the patient;

b) an imaging bladder at least partially disposed about said elongate catheter in spaced relation from said tip of said catheter;

c) an inflation conduit disposed in fluid flow communication with said imaging bladder and structured to direct a fluid into said imaging bladder;

d) said imaging bladder structured to be inflated upon receipt of said fluid, and to engage and substantially conform to at least a portion of a urethral wall;

e) an imaging device including an imaging probe structured to be disposed in operative proximity to said imaging bladder; and f) said imaging device structured to provide a real time image of a vicinity of said imaging probe, said fluid disposed in said imaging bladder structured to define a maintainable acoustic interface with the urethral wall visible utilizing said imaging device so as to identify a boundary of said urethra.

38. A urethral identification system as recited in claim 37 wherein said imaging bladder is formed from a latex free flexible material structured to minimize impedance of said real time image provided by said imaging probe.

39. A urethral identification system as recited in claim 37 wherein said imaging bladder is formed from a flexible latex material.

40. A urethral identification system as recited in claim 37 wherein said imaging bladder includes a wall thickness of between approximately 0.0001 inches to 0.1 inches.

41. A urethral identification system as recited in claim 37 wherein said imaging bladder includes a wall thickness of between approximately 0.001 inches to 0.005 inches.

42. A urethral identification system as recited in claim 37 wherein an inflated diameter of said imaging bladder is approximately 14 Fr–30 Fr.

43. A urethral identification system as recited in claim 37 wherein said fluid is air.

44. A urethral identification system as recited in claim 37 wherein said fluid is a radio-opaque material.

45. A urethral identification system as recited in claim 37 further comprising at least one hyperechoic ring disposed on said catheter.

46. A urethral identification system as recited in claim 37 wherein said imaging bladder is approximately 4 cm in length.

47. A urethral identification system as recited in claim 37 wherein said catheter further comprises a tip bladder disposed generally at said tip of said catheter, said tip bladder structured to be inflated once disposed in the patient's urinary bladder to a size greater than a dimension of an entrance to the urethra from said urinary bladder so as to resist removal of said catheter from said urethra.

48. A urethral identification system as recited in claim 37 wherein said imaging device comprises an ultrasound imaging device.

49. A urethral identification system as recited in claim 48 wherein said imaging probe comprises a transrectal ultrasonography probe structured to be into a rectum of the patient.

50. To be used with an ultrasound device, a urethral identification catheter comprising:

a) an elongate catheter having a primary lumen and a tip structured to be inserted into a patient's urethra in fluid flow communication with a urinary bladder of the patient;

b) a tip bladder structured to be inflated within the patient's urinary bladder to resist removal of said catheter from the urethra;

c) an imaging bladder formed from a flexible material having a wall thickness of approximately 0.0001 inches to 0.1 inches;

d) said imaging bladder at least partially disposed about an exterior of said catheter in spaced relation from said tip bladder;

e) an inflation conduit disposed in fluid flow communication with said imaging bladder and structured to direct a fluid into said imaging bladder;

f) said imaging bladder structured to be inflated upon receipt of said fluid, and to engage at least a portion of a urethral wall in proximity to a prostate of the patient;

g) said imaging bladder and said fluid contained therein structured to define, for an extended and continuos period of time, an acoustic interface with the urethral wall that is visible utilizing the ultrasound device and which identifies a boundary of the urethra.

51. A urethral identification catheter as recited in claim 50 wherein said fluid is air.

52. A urethral identification catheter as recited in claim 50 wherein said imaging bladder includes an inflated diameter of approximately 14 Fr–30 Fr.

53. A urethral identification catheter as recited in claim 50 further comprising at least one at least one hyperechoic ring.

* * * * *